(12) United States Patent
Berkenstam et al.

(10) Patent No.: US 7,238,498 B2
(45) Date of Patent: Jul. 3, 2007

(54) SCREENING METHODS

(75) Inventors: Anders Berkenstam, Stockholm (SE);
Göran Bertilsson, Stockholm (SE);
Lorenz Poellinger, Stockholm (SE)

(73) Assignee: AngioGenetics Sweden AB, Gothenburg (SE)

( * ) Notice: Subject to any disclaimer, the term of this patent is extended or adjusted under 35 U.S.C. 154(b) by 0 days.

(21) Appl. No.: 11/306,504

(22) Filed: Dec. 30, 2005

(65) Prior Publication Data

US 2006/0115849 A1    Jun. 1, 2006

Related U.S. Application Data

(62) Division of application No. 09/896,791, filed on Jun. 29, 2001, now abandoned.

(60) Provisional application No. 60/217,570, filed on Jul. 12, 2000.

(30) Foreign Application Priority Data

Jul. 6, 2000    (SE) .................................. 00025551

(51) Int. Cl.
*C12P 21/06* (2006.01)
(52) U.S. Cl. ................................................... 435/69.1
(58) Field of Classification Search ................ 435/96.7
See application file for complete search history.

(56) References Cited

OTHER PUBLICATIONS

SCORE search results for SEQ ID No. 2, pp. 1-3 (Result 2).*

* cited by examiner

*Primary Examiner*—Karen Cochrane Carlson
*Assistant Examiner*—Agnes B. Rooke
(74) *Attorney, Agent, or Firm*—Todd E. Garabedian; Wiggin and Dana LLP (57) ABSTRACT

A mammalian polypeptide designated Inhibitory PAS Domain Protein (IPAS) is useful for the inhibition of angiogenesis and/or tumor progression. Screening methods exist to identify compounds potentially useful as medicaments for the treatment of medical conditions related to angiogenesis or tumor progression.

6 Claims, 5 Drawing Sheets

SCREENING METHODS

This application is a divisional of 09/896,791 filed on Jun. 29, 2001 now abandoned, which claims benefit of 60/217,570 filed on Jul. 12, 2000.

FIELD OF THE INVENTION

The present invention relates to a mammalian polypeptide designated Inhibitory PAS Domain Protein (IPAS) which polypeptide is useful for the inhibition of angiogenesis and/or tumor progression. The invention also relates to screening methods for compounds potentially useful as medicaments for the treatment of medical conditions related to angiogenesis or tumor progression.

BACKGROUND OF THE INVENTION

Oxygen plays a critical biological role as the terminal electron acceptor in the mitochondria of vertebrate cells. During evolution, these cells have developed ways to sense alterations in oxygen levels and, during this process, acquired the ability to conditionally modulate the expression of genes involved in adaptive physiological responses to hypoxia including angiogenesis, erythropoiesis, and glycolysis. These genes include vascular endothelial growth factor, eryhtropoietin, several glycolytic enzymes and inducible nitric oxide synthase, and have all been shown to contain hypoxia responsive elements (HREs). Under hypoxic conditions these response elements are recognized by a heterodimeric complex consisting of the hypoxia inducible factor-1a (HIF-1a) and Arnt. Both these transcription factors belong to the rapidly growing family of basic-helix-loop-helix (bHLH)-PAS (Per, Arnt, Sim) proteins.

A family of helix-loop-helix proteins designated Id has been identified as antagonists of bHLH transcriptional regulators. bHLH proteins typically bind regulatory sequences in a heterodimeric configuration and function to activate differentiation-linked gene expression. The heterodimer usually comprises a class A bHLH protein together with a class B bHLH protein. In the presence of excess Id protein, the class A bHLH partner is typically titrated out through heterodimerization with Id protein.

Dysregulation or overfunction of HIF-1 a might cause a variety of pathological conditions including tumor progression and inflammatory angiogenesis. Consequently, there is a need for identification of compounds acting as negative regulators of HIF-1a, said compounds being potentially useful against medical conditions related to angiogenesis and tumor progression.

DESCRIPTION OF THE DRAWINGS

(b) Schematic representation of structural features of IPAS and the hypoxia-inducible factors. The percent identities of each protein with IPAS within the bHLH and PAS motifs are shown. bHLH, basic helix-loop-helix; PAS, Per/Arnt/Sim; N- or C-TAD, N- or C-terminal transactivation domain.

(c) Northern blot analysis of IPAS expression in adult mouse tissues. Poly(A)$^+$ RNA (4.5 micro grams) from various adult mouse tissues were hybridized with 32P-labeled IPAS cDNA probe. The positions of RNA markers are shown on the right in kb.

(d)-(o) In situ hybridization analysis. Sections of cornea (d-g), retina (h-k), and cerebellum (l-o) of adult mouse were hybridized with antisense RNA probes of mIPAS (d, e, h, i, l, and m) or mHIF-1a (f, g, j, k, n, and o). Light-(d, f, h, j, l, and n) and dark-field (e, g, i, k, m, and o) views are shown. C, cornea; Ep, epithelium; S, substantia propria; LE, lens epithelium; GC, granular cell layer; INL, inner nuclear layer; R&C, rods and cones, G, granular layer; P, Purkinje cells; M, molecular layer.

(b), (c) IPAS inhibits hypoxia-inducible factors-mediated gene expression. IPAS expression vector, HRE-luciferase reporter, and HIF-1a (b) or HLF (c) expression vector (CMV HIF-1a or CMV HLF, respectively) were introduced into HeLa cells. After 24 hours incubation in normoxic (21% O2) or hypoxic (1% O2) condition, luciferase activity was measured. Results were expressed as fold induction compared with the luciferase activity in the cells transfected with reporter gene alone. Means +/–SD were shown.

(d) IPAS does not affect on HIF-1a and HLF protein levels. HeLa cells were transfected with FLAG-tagged IPAS expression plasmid (1.0 micro grams/21.5 cm2 dish) and exposed to hypoxia for 6 h. Whole cell extracts (50 micro grams) were prepared and subject to immunoblot analysis using antibodies against HIF-1a (Novus), HLF (Novus), and FLAG epitope (Sigma) essentially as previously described.

(b) Inhibition of hypoxia-inducible gene expression by IPAS at transcriptional level. HRE-luciferase reporter was transfected with or without HIF-1a expression vector into Hepa1c1c7 or Hepa IPAS cells. The cells were cultured under conditions of either 21% or 1% O2 concentration and subject to luciferase assay. Luciferase content of the Hepa1c1c7 cells transfected with the reporter gene alone was served as a control and results were shown as fold induction compared with the control.

(c) IPAS inhibits the binding of HIF-1a/Arnt complex to HRE. Nuclear extracts from normoxic or hypoxic Hepa1c1c7 and Hepa IPAS cells were analyzed by EMSA using 32P-labelled HRE oligonucleotide probe. The asterisks show position of constitutive HRE-binding activity in the nuclear extracts and arrow shows the position of hypoxia-induced HIF-1a/Arnt-DNA complex. Competition assay by unlabelled HRE (S) or unrelated sequence(NS) and supershift formation by anti HIF-1a antibody and anti-Arnt antibody were shown.

(d) IPAS does not affect on dioxin-inducible gene expression. Hepa1c1c7 and Hepa IPAS cells were treated with or without TCDD (10 nM) for 24 h and poly(A)+RNA from the cells was 30 hybridized with 32P-labelled mouse CYP1A1, IPAS, and beta-actin cDNA probe.

(e) IPAS has no effect on TCDD-mediated XRE-reporter gene expression. Hepa1c1c7 and Hepa IPAS cells were transfected with XRE-reporter plasmid and after incubation with or with out TCDD for 24 h luciferase activity was monitored. Results were expressed as fold induction of luciferase activity compared to the ligand free control of Hepa1c1c7 cells. Means +/−SD were shown.

(b) The N-terminal structure of HIF-1a is essential for the heterodimerization with IPAS. 35S-labelled, in vitro translated IPAS was incubated with GAL4-fusion of various fragments of HIF-1a and subject to the immunoprecipitation with either anti GAL4 antibody or preimmune control serum. Precipitated fraction was analyzed by SDS PAGE and results were obtained by autoradiography. Ten percent of input IPAS was shown as a control.

(c), (d) In vivo interaction between IPAS and HIF-1a. COS7 cells were transfected with various amounts of expression vectors for GAL4-HIF-1a/1-330 and VP16-IPAS (c) or GAL4-IPAS and VP16-Arnt (d) as indicated together with GAL4-driven reporter gene. After 24 hours incubation, cellular luciferase activity was determined. Results were expressed as fold induction compared with the luciferase contents of the cells transfected with reporter gene alone.

(e) IPAS/HIF-1a heterodimer fails to bind to HRE. Various combinations of in vitro translated IPAS, HIF-1a, and Arnt, or unprogrammed reticulocyte lysate as indicated were mixed with $^{32}$P-labelled HRE oligonucleotide probe, and the protein-DNA complex formation was s monitored by EMSA. Results were visualized by autoradiography.

FIG. 5: Involvement of IPAS in silencing the production of angiogenic growth factor in cornea epithelium cells Primary culture of mouse cornea epithelium cells were transfected with either antisense IPAS expression plasmid or empty vector (vector) and incubated under normoxic (N, 21% O2) or hypoxic (H, 1% O2) conditions for 24 h. Total RNAs from the cells were extracted and Northern blot analysis using radiolabelled mouse VEGF cDNA probe was performed. Total RNAs form normoxic and hypoxic Hepa1c1c7 cells were supplied as a reference for VEGF induction. As a loading control, 18S RNA levels are shown.

DETAILED DESCRIPTION

The present invention provides a model wherein activated HIF-1a encounters a negative regulation by a small protein factor such as IPAS, to form a nonfunctional heterodimeric complex. This mode of regulation of HIF-1a might contribute to a fine-tuning of hypoxia signalling in situas evidenced by profound negative effect of IPAS in corneal VEGF production. On the other hand, ectopic expression of IPAS potentially repressed hypoxia-inducible VEGF expression, and the negative effect of IPAS was selective to hypoxia signalling so far tested. Therefore, it is postulated that IPAS is useful as a target in therapeutic drug design for various angiogenic diseases, such as ischemic cardiovascular lesions, stroke, and diabetic microvascular diseases.

Consequently, in a first aspect this invention provides an isolated nucleic acid molecule selected from:

nucleic acid molecules comprising a nucleotide sequence set forth as SEQ ID NO: 2;

nucleic acid molecules comprising a nucleotide sequence capable of hybridizing, under stringent hybridization conditions, to a nucleotide sequence complementary the polypeptide coding region of a nucleic acid molecule as defined in (a) and which codes for a biologically active mammalian IPAS polypeptide or a functionally equivalent modified form thereof; and nucleic acid molecules comprising a nucleic acid sequence which is degenerate as a result of the genetic code to a nucleotide sequence as defined in (a) or (b) and which codes for a biologically active mammalian IPAS polypeptide or a functionally equivalent modified form thereof.

The nucleic acid molecules according to the present invention include cDNA, chemically synthesized DNA, DNA isolated by PCR, genomic DNA, and combinations thereof. Genomic DNA may be obtained by screening a genomic library with the IPAS cDNA described herein, using methods that are well known in the art. RNA transcribed from DNA is also encompassed by the present invention.

The term "stringent hybridization conditions" is known in the art from standard protocols and could be understood as e.g. hybridization to filter-bound DNA in 0.5 M NaHPO4, 7% sodium dodecyl sulfate (SDS), 1 mM EDTA at +65° C., and washing in 0.1×SSC/0.1% SDS at +68° C.

In a preferred form of the invention, the said nucleic acid molecule has a nucleotide sequence identical with SEQ ID NO: 2 ofthe Sequence Listing. However, the nucleic acid molecule according to the invention is not to be limited strictly to the sequence shown as SEQ ID NO: 2. Rather the invention encompasses nucleic acid molecules carrying modifications like substitutions, small deletions, insertions or inversions, which nevertheless encode proteins having substantially the biochemical activity of the IPAS polypeptide according to the invention. Included in the invention are consequently nucleic acid molecules, the nucleotide sequence of which is at least 90% homologous, preferably at least 95% homologous, with the nucleotide sequence shown as SEQ ID NO: 2 in the Sequence Listing.

Included in the invention is also a nucleic acid molecule which nucleotide sequence is degenerate, because of the genetic code, to the nucleotide sequence shown as SEQ ID NO: 2. A sequential grouping of three nucleotides, a "codon" , codes for one amino acid. Since there are 64 possible codons, but only 20 natural amino acids, most amino acids are coded for by more than one codon. This natural "degeneracy" , or "redundancy" , of the genetic code is well known in the art. It will thus be appreciated that the nucleotide sequence shown in the Sequence Listing is only an example within a large but definite group of sequences which will encode the IPAS polypeptide.

In a further aspect, this invention provides an isolated mammalian IPAS polypeptide encoded by the nucleic acid molecule as defined above. In a preferred form, the said polypeptide has an amino acid sequence according to SEQ ID NO: 3 of the Sequence Listing. However, the polypeptide according to the invention is not to be limited strictly to a polypeptide with an amino acid sequence identical with SEQ ID NO: 3 in the Sequence Listing. Rather the invention encompasses polypeptides carrying modifications like substitutions, small deletions, insertions or inversions, which polypeptides nevertheless have substantially the biological activities of the IPAS polypeptide. Included in the invention are consequently polypeptides, the amino acid sequence of which is at least 90% homologous, preferably at least 95% homologous, with the amino acid sequence shown as SEQ ID NO: 3 in the Sequence Listing.

In yet another aspect, the invention provides a vector comprising the nucleic acid sequence as defined above. The term "vector" refers to any carrier of exogenous DNA that is useful for transferring the DNA to a host cell for replication and/or appropriate expression of the exogenous DNA by the host cell. The said vector can be a replicable expression vector, which carries and is capable of mediating the expression of a nucleic acid sequence according to the invention. In the present context, the term "replicable" means that the vector is able to replicate in a given type of host cell into which it has been introduced. Examples of vectors are viruses such as bacteriophages, cosmids, plasmids and other recombination vectors. Nucleic acid molecules are inserted into vector genomes by methods well known in the art.

Included in the invention is also a cultured host cell harboring a vector according to the invention. Such a host cell can be a prokaryotic cell, a unicellular eukaryotic cell or a cell derived from a multicellular organism. The host cell can thus e.g. be a bacterial cell such as an *E. coli* cell; a cell from a yeast such as *Saccharomyces cervisiae* or *Pichia pastoris*, or a mammalian cell. The methods employed to effect introduction of the vector into the host cell are standard methods well known to a person familiar with recombinant DNA methods. The invention also includes a process for production of a mammalian IPAS polypeptide, comprising culturing the said host cell under conditions whereby said polypeptide is produced, and recovering said polypeptide, In a further important aspect, the invention provides a (screening) method for identifying is an agent useful for activating the expression of a mammalian IPAS nucleic acid molecule, said method comprising the steps contacting a candidate agent with a mammalian IPAS nucleotide acid molecule, or with a mammalian IPAS polypeptide, according to the invention; and determining whether said candidate agent activates the expression of the said 20 mammalian IPAS nucleic acid molecule, or stimulates the biological activities of the said polypeptide.

For screening purposes, appropriate host cells can be transformed with a vector having a reporter gene under the control of the TAS gene according to this invention. The expression of the reporter gene can be measured in the presence or absence of an agent with known activity (i.e. a standard agent) or putative activity (i.e. a "test agent" or "candidate agent"). A change in the level of expression of the reporter gene in the presence of the test agent is compared with that affected by the standard agent. In this way, active agents are identified and their relative potency in this assay determined.

As used herein, the term "reporter gene" means a gene encoding a gene product that can be identified using simple, inexpensive methods or reagents and that can be operably linked to an IPAS sequence. Reporter genes such as, for example, a luciferase, P-galactosidase, alkaline phosphatase, or green fluorescent protein reporter gene, can be used to determine transcriptional activity in screening assays according to the invention.

As used herein, the term "agent" means a biological or chemical compound such as a simple or complex organic molecule, a peptide, a protein or an oligonucleotide. Such an agent, identified in the methods according to the invention, is potentially useful e.g. in the identification, development and manufacture of medicaments for the inhibition of angiogenesis and/or tumor growth, including angiogenic diseases related to ischemic cardiovascular lesions, stroke, or diabetic microvascular diseases.

Consequently, the invention also provides other researchers with a method for the treatment of angiogenic disease or tumor growth, comprising administering to a subject an effective amount of an agent identified by the method described above. The term "treatment" means any treatment of a disease in a mammal, including: (i) preventing the disease, i.e. causing the clinical symptoms of the disease not to develop; (ii) inhibiting the disease, i.e. arresting the development of clinical symptoms; and/or (iii) relieving the disease, i.e. causing the regression of clinical symptoms. The term "effective amount" means a dosage sufficient to provide treatment for the disease state being treated. This will vary depending on the patient, the disease and the treatment being effected.

Throughout this description the terms "standard protocols" and "standard procedures", when used in the context of molecular biology techniques, are to be understood as protocols and procedures found in an ordinary laboratory manual.

Plasmid Construction pcDNA3 IPAS was made by insertion of the EcoRI-NotI fragment from pT7T3D IPAS (GenBank Acc: AA028416) into EcoRI-NotI digested pcDNA3 plasmid (Invitrogen). PCMV IPAS or pFLAG IPAS contained HindIII-XbaI orBamHI-XbaI fragment pcDNA3 IPAS in corresponding site of pCMV4 or pCMV FLAG plasmid, respectively. HRE-luciferase, XRE-luciferase, and PCMV HIF-1a are described elsewhere. pBluescript mHLF was gift from Dr. Y. Fujii-Kuriyama and used for construction of pCMV mHLF. For the construction of the pGST, a plasmid for in vitro translation of GST-fusion protein, GST cDNA and multiple cloning site of pGEX-4T-3 (Amersham Pharmacia Biotech) was amplified by PCR with BgII and HindIII linker, and subcloned into BglI-HindIII site of pSP72 vector (Promega). PGST IPAS was made by insertion of PCR-cloned IPAS cDNA with BamHI and XhoI linker into BamHI-XhoI-digested PGST. GAL4 HIF-1a/1-826, 1-330, 1-652, 526-826 were as previously described. For pCMX GAL4-IPAS or pCMX VP-16 IPAS construction, EcoRI-XbaI orBamHI-XbaI fragment of pcDNA3 IPAS was inserted into EcoRI-NheI site of pCMX GAL4 or to BamHI-NheI site of pCMX VP16, respectively. PCMXVP16-Arnt was gift from Dr. I. Pongratz. To make antisense IPAS expression plasmid, full length IPAS cDNA with EcoRI-BamHI linker was inserted in inverted direction to BamHI-EcoRI site of pcDNA3 plasmid.

Cell Culture and Transfection

Hepa1c1c7, HeLa, and COS7 cells were from ATCC. Hepa IPAS cells were established by stable transfection of Hepa1c1c7 cells with pEFIRESpuro IPAS and puromycin (5 micro grams/ml) selection. Transient transfections were carried out by the lipofection procedure in 28 cm2 culture plates. In luciferase assay, 0.5 micro grams of reporter plasmids and indicated amounts expression plasmids were transfected. Hypoxic- or TCDD treatment of the cells was previously described.

Northern Blot and In Situ Hybridization Analysis

Poly(A)+ RNAs (4.5 micro grams) from various tissues of 8 week-old C5 7B1 6 mice or Hepa1c1c7 and Hepa IPAS cells were obtained by guanidiumthiocyanate methods followed by oligo dT-beads purification (Dynal) and analyzed by Northern blot using 32P-labelled cDNA probes of mIPAS (nt 623-897), mPGKI (nt 426-771), mVEGF3 (nt 24-466), mCYP1A1(nt 874-1199), and (beta-actin (nt 930-1075). Total RNA (20 micro grams) from mouse corneal epithelium primary culture or Hepa1c1c7 cells was separated and probed with radiolabelled mVEGF3 cDNA (nt 24-466) probe. In situ hybridization of tissue sections from 8 week-old C57B16 mice using 35S-labelled mIPAS or mHIF-1a antisense RNA probe was performed as previously described.

Electrophoretic Mobility Shift Assay

Nuclear extracts from either normoxic or hypoxic cells were prepared as described before. Ten microgram of the nuclear extract was incubated with 32P-labelled HRE oligonucleotide in a buffer containing 0.1 micro grams of sonicated, denatured calf thymus DNA in 10 mM Tris-HCl (pH 7.5), 60 mM KCl, 50 mM NaCl, 1 mM MgCl2, 1 mM EDTA, 5 mM dithiothreitol (DTT), 5% glycerol. Various combination of in vitro translated proteins (5 micro liters each) were mixed with HRE probe in a solution containing 10 mM Hepes, 100 mM KCL, 0.1 mM EDTA, 3 mM MgCl2, 4 mM spermidine, 0.5 mM DTT, 10% glycerol, 20 ng/µl tRNA, 1 ng/micro liters salmon-sperm DNA. The protein-DNA complexes were separated on 4% polyacrylamid gel in 0.5× TBE buffer (IxTBE; 89 mM Tris, 89 mM Boric acid, 5 mM EDTA).

In Vitro Protein Interaction Assay

GST-fused IPAS or GALA-fusion of various fragments of HIF-1a were generated by translation either in the presence or absence of 35S-labeled methionine in rabbit reticulocyte lysate (Promega). Protein concentration of GST-IPAS or GAL4-HIF-1 as was determined on the basis of incorporated 35S-labeled methionine. Equal amount of 35S-labeled, in vitro translated Arnt, HIF-1a or IPAS were incubated with GST IPAS or GAL4-HIF-1 as for 1 h at room temperature, followed by incubation with anti-GST antibody (Amersham Pharmacia Biotech) or anti-GAL4 antibody (Upstate Biotechnology) conjugated Protein A Sepharose (Amersham Pharmacia biotech) for another 1 h at room temperature. After brief centrifugation, coimmunoprecipitated proteins were analyzed by SDS-PAGE.

Isolation of Murine Corneal Epithelial Cells

Six-week-old C57B16/J healthy mice were killed with a lethal dose of CO2. The eyes were enucleated and the corneal tissue was dissected in DME medium supplemented with 10% bovine calf serum under a stereomicroscope. The corneal tissue was cut into small pieces under sterile conditions and washed with DMEM twice. The tissue masses were placed onto a gelatin-coated tissue culture plate and incubated in DMEM with 10% bovine calf serum supplemented with human recombinant FGF-beta at the concentration of 3 ng/ml. After incubation in 5% CO2 for 8 days, corneal epithelial cells grown to nearly confluence were trypsinized. A single cell suspension was then seeded onto 21.5 cm2 culture dishes and cells were grown under the same condition as described above.

EXAMPLE 1

Identification of IPAS Sequence

Hidden Markov Model profiles were designed using the HMMER 1,8,3 software from nucleotide sequences corresponding to the PAS domain of a selected number of bHLH/PAS factors. A mouse EST database at GenBank (http.//www.ncbi.nlm.nih.gov) was screened and an EST clone of 460 bp (GenBank Acc: AA028416; SEQ ID NO: 1) containing a bHLH (basic-helix-loop-helix) PAS motif, was identified.

Figure 1:
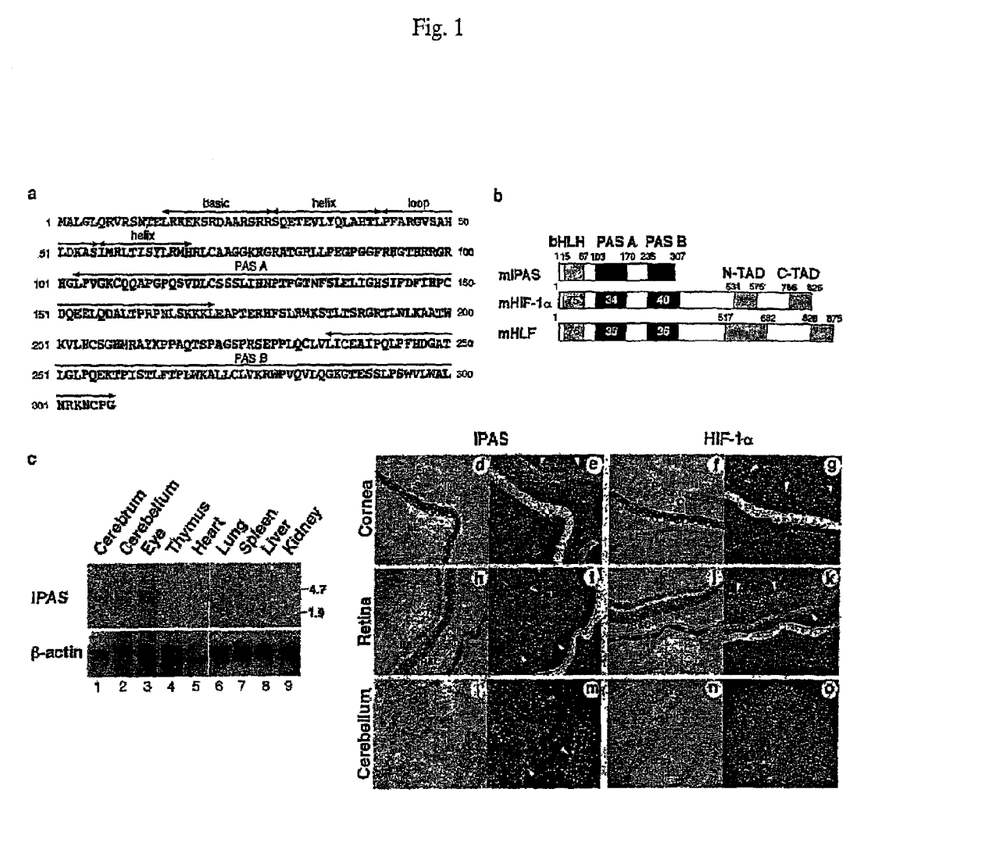
FIG. 1: Mouse IPAS sequence and expression (a) Deduced amino acid sequence of mouse IPAS. Domains of basic helix-loop-helix and PAS A and B are shown.

DNA sequence analysis revealed that IPAS cDNA (SEQ ID NO: 2) contains an open reading frame of 921 nucleotides, encoding a polypeptide of 307 amino acids (FIG. 1a; SEQ ID NO: 3). The predicted polypeptide was designated IPAS (Inhibitory PAS Domain Protein).

Alignment analysis of this amino acid sequence with known bHLH PAS factors showed high similarity to HIF-1a and HLF in the N-terminal bHLH domain (75% and 76% identity, respectively; FIG. 1b), and to a lesser extent within PAS region (34% and 36% in the PAS A, and 40% and 36% in the PAS B domain, respectively; FIG. 1b). Notably, IPAS lacks the sequence corresponding to C-terminal region of HIF-1a and RLF, in which two transactivation domains (NTAD and CTAD) have been identified.

EXAMPLE 2

IPAS mRNA is Expressed Predominantly in the Eye

Northern blot analysis of poly(A)+ RNA from a variety of mouse tissues demonstrated that IPAS mRNA was expressed predominantly in the eye and at lower levels in the cerebellum and the cerebrum. No obvious expression in was detected in other tested mouse tissues, indicating a very tissue-restricted expression pattern of IPAS mRNA (FIG. 1c).

EXAMPLE 3

IPAS expression is Observed in the Epithelial Cell Layer of the Cornea

To characterize the spatial expression pattern of the TAS gene in the eye and cerebellum, in situ hybridization was performed. Intense IPAS expression was observed in the epithelial cell layer of the cornea (FIGS. 1d and 1e) and with lower intensity in the layers of ganglion cells, inner nuclear cells, and rods and cones of the retina (FIGS. 1h and 1i).

Expression of HIF-1a mRNA was detected by in situ hybridization at low levels in the epithelium of the cornea (FIGS. 1f and 1g), demonstrating remarkably dominant expression of IPAS over HIF-1a in these cells. HIF-1a was also expressed in the same layers of retina where IPAS expression was observed (FIGS. 1j and 1k), In the cerebellum, expression of IPAS was limited to the Purkinje cell layer (FIGS. 1l and 1m), whereas HIF-1a did not show any localized expression throughout the sections (FIGS. 1j and 1k). Both IPAS and HIF-1a mRNAs were observed as weak diffuse signal over nonspecific background levels in certain areas of the cerebrum (data not shown).

EXAMPLE 4

Figure 2:
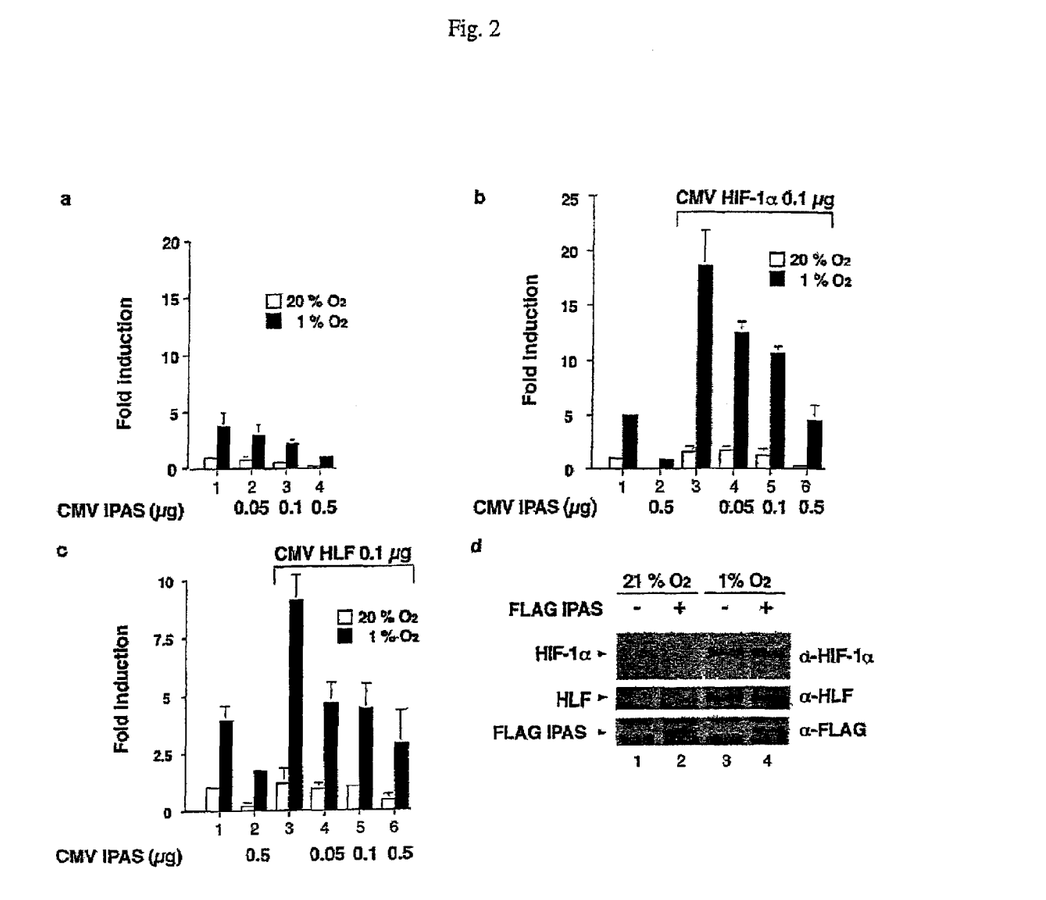
FIG. 2: IPAS is a dominant negative regulator of hypoxia-inducible factors (a) IPAS does not transactivate HRE-driven reporter gene. Increasing amounts of IPAS expression vector (CMV IPAS) were cotransfected with HRE-luciferase reporter gene into HeLa cells. The cells were cultured under either normoxic (21% O2) or hypoxic (1% O2) conditions for 24 h and the cellular luciferase expression was determined.

Coexpression of TAS Reduces Hypoxia-Inducible Reporter Gene Expression in HeLa Cells The structural similarity of IPAS to hypoxia-inducible transcription factors and the colocalization of IPAS and HIF-1a in mouse cornea prompted us to investigate the role of IPAS in transcriptional control of cellular responsiveness to hypoxia. We performed in HeLa cells a transient transfection assay using a hypoxia-response element-(HRE-) driven luciferase reporter in the absence or presence of transiently expressed IPAS. Incubation of the cells under hypoxic (1% O2) conditions induced 4.2-fold activation of the reporter gene, representing the induced transactivation function of endogenous hypoxia-inducible factors (FIG. 2a). Coexpression of IPAS reduced hypoxia-inducible reporter gene in HeLa cells stimulated to a high level of luciferase expression in hypoxia-dependent manner (FIGS. 2b and FIG. 2c, respectively), indicating that IPAS acts as a dominant negative regulator of the function of endogenous hypoxia-inducible factors. IPAS had no effect on hypoxia-induced protein stabilization of HIF-1a and HLF (FIG. 2d), which has previously been shown to represent a critical initial step in the activation of HIF-1a or HLF function. Thus, IPAS seems to inhibit more down-stream steps in signal transduction mediated by hypoxia-inducible transcription factors.

EXAMPLE 7

Negative Regulation by IPAS is Specific to HIP-Mediated Signalling Pathways

Figure 3:
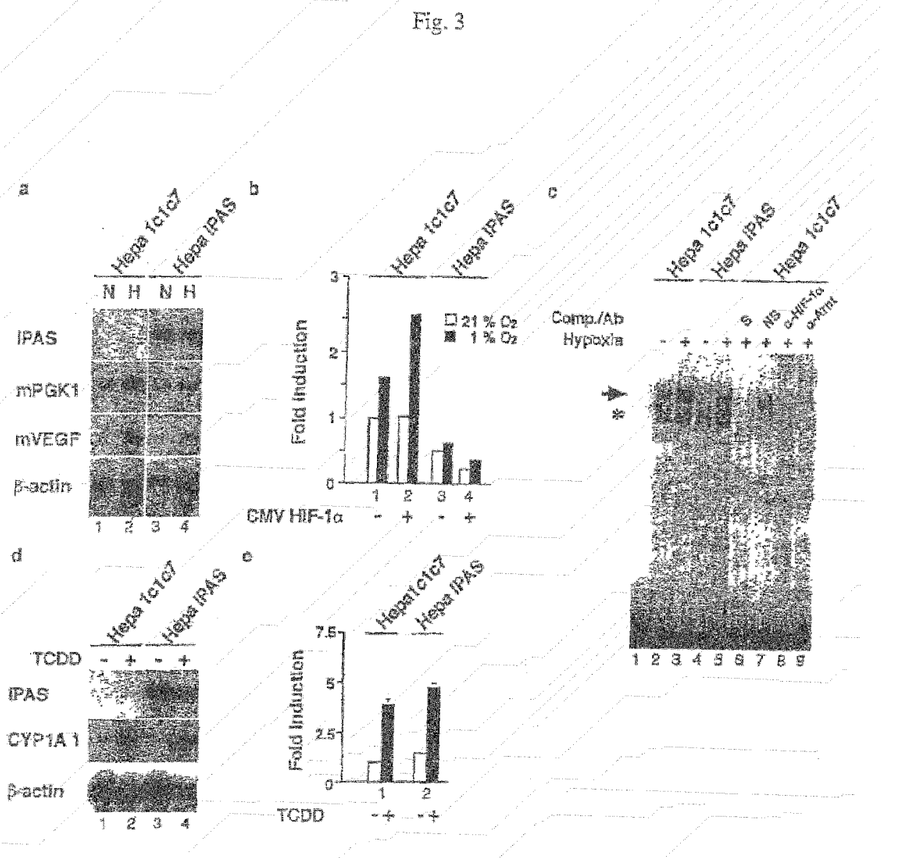
FIG. 3: IPAS specifically attenuates hypoxia inducible mRNAs expression (a) Hypoxia-inducible gene expression is impaired in IPAS overexpressing cells. Wild type (Hepa1 c1 c7) or IPAS-stably transfected (Hepa IPAS) mouse hepatoma cell lines were cultured in either normoxic (N) or hypoxic (H) conditions for 24 h. Poly(A)+RNA from the cells were separated and hybridized with radiolabelled mouse IPAS, PGK1, VEGF, and beta-actin cDNA probe as indicated.

It was examined whether negative regulation by IPAS is specific to HIF-mediated signalling pathways. The aryl hydrocarbon receptor (AhR), which mediates gene regulation in response to xenobiotic chemicals, is also a member of the bHLHIPAS transcription factor family and shares the dimerization partner factor Arnt with HIF-1a. Incubation of the wild-type Hepa 1c1c7 with 2,3,7,8-tetrachlorodibenzo-p-dioxin (TCDD) massively induced mRNA expression of the AhR target gene cytochrome P-4501A1 (CYP1A1). In contrast to hypoxia-inducible gene expression, TCDD-induced expression of CYP1A1 mRNA was unperturbed in Hepa IPAS cells which showed an induction response similar to that observed in wild type cells (FIG. 3d). Consistent with these data, very similar levels of activation of a xenobiotic response element (XRE)-driven reporter gene by the ligand-stimulated AhR/Arnt heterodimeric complex was observed both in the wild type and the IPAS overexpressing Hepa cells (FIG. 3e). Taken together, IPAS seems to preferentially target HIF-1a to act as a dominant negative regulator of hypoxia-inducible gene expression.

EXAMPLE 8

The Inhibitory Action of IPAS is Mediated by Direct Interaction with HIF-1a

Figure 4:
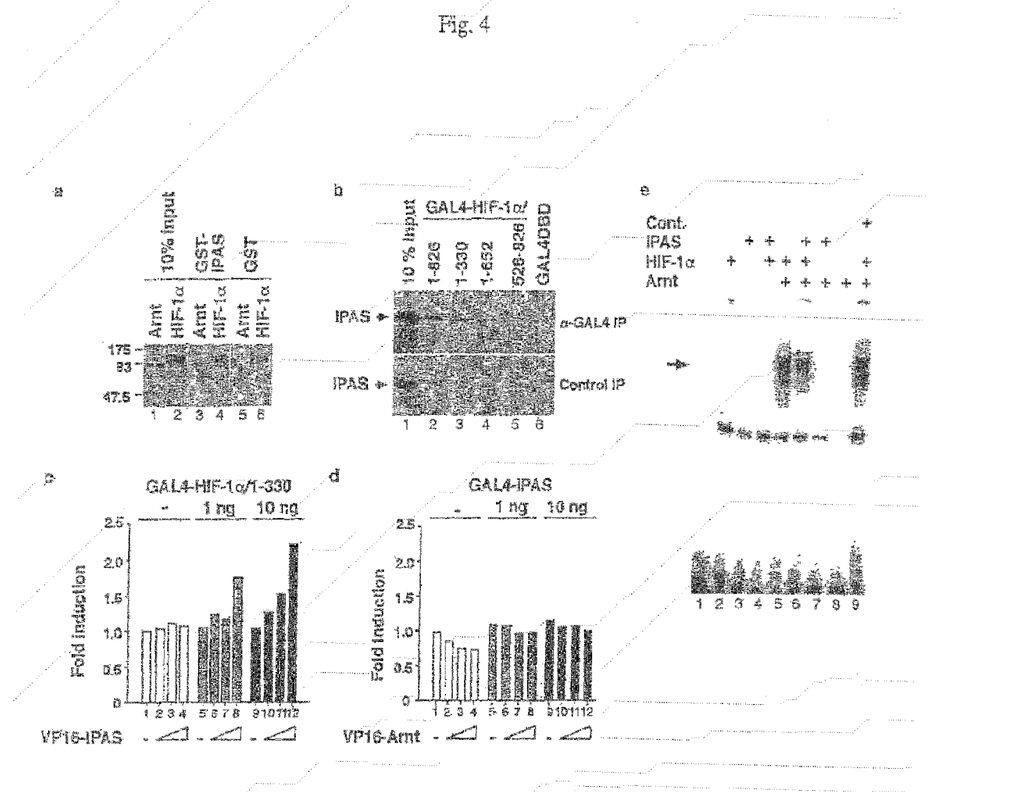
FIG. 4: IPAS targets HIF-1a to form a nonfunctional complex (a) IPAS physically interacts with HIF-1a. In vitro-translated GST-IPAS or GST was mixed with 35S-labelled, in vitro translated Arnt or HIF-1a and immunoprecipitation with anti-GST antibody was carried out. The precipitant was separated by SDS-PAGE followed by autoradiography. For the loading control, 10% of input Arnt and HIF-1a were shown.

It was tested whether the inhibitory action of IPAS is mediated by direct interaction with HIF-1a or Arnt. Radiolabelled, in vitro translated HIF-1a or Arnt were incubated with glutathione S-transferase-(GST-) IPAS fusion proteins and analyzed by immunoprecipitation assays using anti-GST antibodies (Amersham Pharmacia Biotech). GST-IPAS was coprecipitated with HIF-1a but not with Arnt, demonstrating specific physical interaction between IPAS and HIF-1a (FIG. 4a).

EXAMPLE 9

The N-Terminal Part of HIF-1a is Responsible for the Physical Interaction with IPAS To identify the domain of HIF-1a essential for interaction with IPAS, we incubated various fragments of HIF-1a fused to the GAL4 minimal DNA binding domain and radiolabelled IPAS generated by in vitro translation, and immunoprecipitated this material by anti GAL-4 antibodies (Upstate Biotechnology). GAL4-HIF-1a/1-826 (full length), /1-330, and /1-652 clearly coprecipitated IPAS whereas GAL4-HIF-1a/526-826 and GAL4 DBD did not. Together, N-terminal structure of HIF-1 a mainly composed of bHLH/PAS motif is responsible for the physical association with IPAS (FIG. 4b). In support of these observations, mammalian two-hybrid assay employing GAL4-HIF-1a/1-330 and VP16-IPAS demonstrated interaction between IPAS and N-terminal part of HIF-1a in the cells (FIG. 4c). On the other hand, in analogy to the results from pull down assay, GAL-4-IPAS and VP16-Amt failed to show any interaction (FIG. 4d).

EXAMPLE 10

IPAS Inhibits DNA Binding Activity of HIF-1a/Arnt complex

To elucidate the function of IPAS/HIF-1a complex, Electrophoretic Mobility Shift Assay using HRE oligonucleotide probe and in vitro translated proteins was performed. IPAS/HIF-1a heterodimer, as well as HIF-1a or IPAS by itself, was abortive in binding to HRE. Thus IPAS/HIF-1a complex seemed to be inactive in mediating expression of the genes under control of HRE. Moreover, DNA binding activity of HIF-1a/Arnt complex was inhibited by the copresence of IPAS but not by the control translation product (FIG. 4e), indicating that the IPAS/HIF-1a complex might functionally dominate over HIF-1a/Arnt DNA binding complex.

EXAMPLE 11

The N-Terminal Part of HIF-1a is Responsible for the Physical Interaction with IPAS To identify the domain of HIF-1a essential for interaction with IPAS, we incubated various fragments of HIF-1a fused to the GAL4 minimal DNA binding domain and radiolabelled IPAS generated by in vitro translation, and immunoprecipitated this material by anti GAL-4 antibodies (Upstate Biotechnology). GAL4-HIF-1a/1-826 (full length), /1-330, and /1-652 clearly coprecipitated IPAS whereas GAL4-HIF-1a/526-826 and GAL4 DBD did not. Together, N-terminal structure of HIF-1a mainly composed of bHLH/PAS motif is responsible for the physical association with IPAS (FIG. 4b). In support of these observations, mammalian two-hybrid assay employing GAL4-HIF-1a/1-330 and VP16-IPAS demonstrated interaction between IPAS and N-terminal part of HIF-1a in the cells (FIG. 4c). On the other hand, in analogy to the results from pull down assay, GAL-4-IPAS and VP16-Amt failed to show any interaction (FIG. 4d).

EXAMPLE 12

IPAS Inhibits DNA Binding Activity of HIF-1a/Arnt Complex

To elucidate the function of IPAS/HIF-1a complex, Electrophoretic Mobility Shift Assay using HRE oligonucleotide probe and in vitro translated proteins was performed. IPAS/HIF-1a heterodimer, as well as HIF-1a or IPAS by itself, was abortive in binding to HRE. Thus IPAS/HIF-1a complex seemed to be inactive in mediating expression of the genes under control of HRE. Moreover, DNA binding activity of HIF-1a/Arnt complex was inhibited by the copresence of IPAS but not by the control translation product (FIG. 4e), indicating that the IPAS/HIF-1a complex might functionally dominate over HIF-1a/Arnt DNA binding complex.

EXAMPLE 13

Introduction of IPAS Antisense into Cornea Cells Stimulates Expression and Hypoxia Inducibility of the VEGF Gene What is the significance of dominant negative function of IPAS in hypoxia signalling and its massive expression in, for example, cornea epithelium? A hallmark of normal cornea is a total avascularity and maintenance of transparency is essential to corneal function. By an overnight eye closure, corneal environment can be enough hypoxic to stimulate hypoxia-inducible gene expression, however, neovascularization in cornea is usually prevented although underlying mechanisms are unknown.

Figure 5:
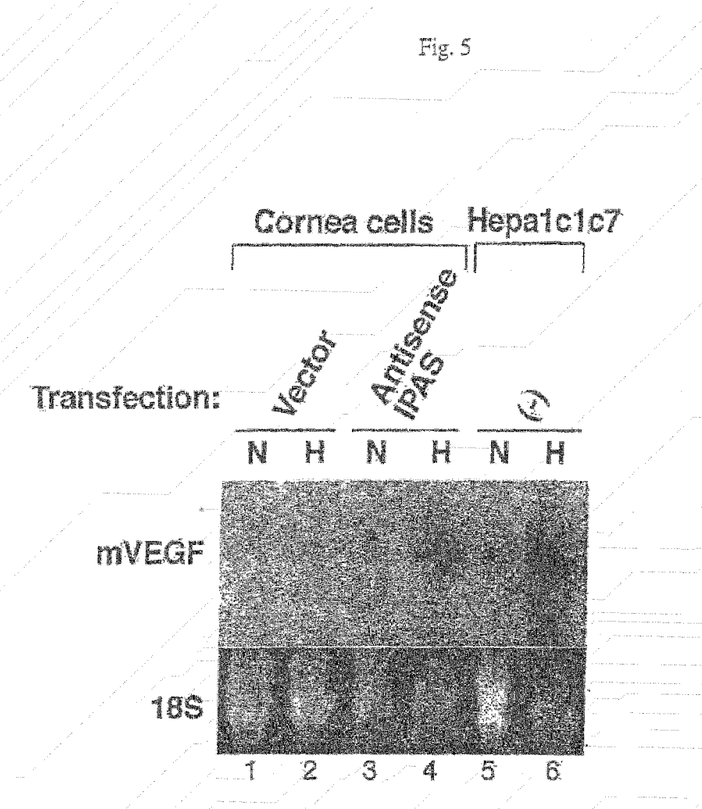

Given the fact IPAS down regulates hypoxia-responsive VEGF expression, we tried to elucidate the effect of IPAS on hypoxia-inducible VEGF expression in cornea. For this purpose, a primary culture of the cornea epithelium cells was transfected with antisense IPAS expression plasmid (or control empty vector) to manipulate IPAS level and incubated with or without hypoxic stimulation for 24 h, thereafter VEGF mRNA expression was monitored in comparison with hepatoma cell lines by Northern Blotting. Hepatoma cell lines showed high level induction of VEGF by hypoxic treatment as previously shown (FIG. 5). In sharp contrast, cornea cells transfected with control vector demonstrated low basal level and modest induction of VEGF expression by hypoxia, which might represent the mechanism for a low profile of corneal angiogenesis. Strikingly, introduction of IPAS antisense into the cornea cells recovered both basal expression and hypoxia inducibility of VEGF gene (FIG. 5), indicating that IPAS may have an important role in silencing angiogenic VEGF expression in cornea especially in hypoxic conditions.

REFERENCES

Bunn, H. F. & Poyton, R. O. Oxygen sensing and molecular adaptation to hypoxia. *Physiol Rev* 76, 839-885 (1996).

Wenger, R. H. Mammalian oxygen sensing, signalling and gene regulation. *J. Exp. Biol.* 203, 1253-1263 (2000).

Krogh, A., Brown, M., Mian, I. S., Sjolander, K. & Haussler, D. Hidden Markov models in computational biology. Applications to protein modeling. *J. Mol. Biol.* 235, 1501-1531 (1994).

Wang, G. L., Jiang, B. H., Rue, E. A. & Semenza, G. L. Hypoxia-inducible factor 1 is a basic-helix-loop-helix-PAS heterodimer regulated by cellular 02 tension. *Proc Natl Acad Sci USA* 92, 5510-5514 (1995).

Ema, M. et al. A novel bHLH-PAS factor with close sequence similarity to hypoxia-inducible factor 1alpha regulates the VEGF expression and is potentially involved in lung and vascular development. *Proc Natl Acad Sci USA* 94, 4273-4278 (1997).

Kallio, P. J., Wilson, W. J., OBrien, S., Makino, Y. & Poellinger, L. Regulation of the hypoxia-inducible transcription factor 1alpha by the ubiquitin-proteasome pathway. *J Biol Chem* 274, 6519-6525 (1999). See also International Patent Application WO 00/29437.

Maxwell, P. H. et al. The tumour suppressor protein VHL targets hypoxia inducible factors for oxygen-dependent proteolysis [see comments]. *Nature* 399, 271-275 (1999).

Wiesener, M. S. et al. Induction of endothelial PAS domain protein-1 by hypoxia: characterization and comparison with hypoxia-inducible factor-Ia. *Blood* 92, 2260-2268 (1998).

Li, H., Ko, H. P. & Whitlock, J. P. Induction of phosphoglycerate kinase 1 gene expression by hypoxia. Roles of Arnt and HIF1 alpha. *J Biol Chem* 271, 21262-21267 (1996).

Forsythe, J. A. et al Activation of vascular endothelial growth factor gene transcription by hypoxia inducible factor 1. *Mol. Cell Biol.* 76, 4604-4613 (1996).

Poellinger, L. in Inducible gene expression (ed. Baeuerle, P. A.) 177-205 (Birkhäuser, Boston, 1995).

Gradin, K. et al. Functional interference between hypoxia and dioxin signal transduction pathways: competition for recruitment of the Arnt transcription factor. 30 *Mol Cell Biol* 16, 5221-5231 (1996).

Thakur, A., Willcox, M. D. & Stapleton, F. The proinflammatory cytokines and arachidonic acid metabolites in human overnight tears: homeostatic mechanisms. *J. Clin. Immunol.* 18, 61-70 (1998).

Sack, R. A., Beaton, A. R. & Sathe, S. Diurnal variations in angiostatin in human tear fluid: a possible role in prevention of corneal neovascularization. *Curr. Eye. Res* 18, 186-193 (1999).

Ravi, R. et al. Regulation of tumor angiogenesis by p53-induced degradation of hypoxia-inducible factor Ia. *Genes Dev.* 14, 34-44 (2000).

Zundel, W. et al Loss of PTEN facilitates HIF-1-mediated gene expression. *Genes Dev.* 14, 391-396 (2000).

Li, J. et al. PR 39, a peptide regulator of angiogenesis. *Nat. Med.* 6, 49-55 (2000).

Norton, J. D., Deed, R. W., Craggs, G. & Sablitzky, F. Id helix-loop-helix protein in cell growth and differentiation. *Trends Cell Biol.* 8, 58-65 (1998).

Eddy, S. R. Multiple alignment using hidden Markov models. *Ismb* 3, 114-120 (1995).

Kallio, P. J. et al Signal transduction in hypoxic cells: inducible nuclear translocation and recruitment of the CBP/p300 coactivator by the hypoxia inducible factor-1alpha. *Embo J* 17, 6573-6586 (1998).

Bertilsson, G. et al. Identification of a human nuclear receptor defines a new signalling pathway for CYP3A induction. *Proc. Nat Acad. Sci. USA* 95, 12208-12213 (1998).

What is claimed is:

1. An isolated nucleic acid molecule selected from:
   (a) nucleic acid molecule comprising a nucleotide sequence set forth as SEQ ID NO: 2;
   (b) nucleic acid molecule comprising a nucleotide sequence capable of hybridizing, under stringent hybridization conditions comprising 0.5 M NaHPO$_4$, 7% sodium dodecylsulfate (SDS), 1 mM EDTA at 65° C., to a nucleotide sequence complementary to the polypeptide coding region of a nucleic acid molecule as defined in (a) and wherein the nucleic acid molecule codes for a biologically active mammalian Inhibitory Per-Arnt-Sim (IPAS) polypeptide that inhibits angiogenesis and/or tumor progression; and
   (c) nucleic acid molecule comprising a nucleic acid sequence which is degenerate as a result of the genetic code to a nucleotide sequence as defined in (a) or (b) and wherein the nucleic acid molecule codes for a biologically active mammalian IPAS polypeptide.

2. A vector comprising the nucleic acid sequence as defined in claim 1.

3. A cultured host cell harboring a vector according to claim 2.

4. A replicable expression vector, which carries and is capable of mediating the expression of a nucleic acid sequence as defined in claim 1.

5. A cultured host cell harboring a vector according to claim 4.

6. A process for production of IPAS polypeptide, comprising culturing a host cell according to claim 3 under conditions whereby said polypeptide is produced, and recovering said polypeptide.

* * * * *

UNITED STATES PATENT AND TRADEMARK OFFICE
CERTIFICATE OF CORRECTION

PATENT NO.       : 7,238,498 B2                                   Page 1 of 1
APPLICATION NO.  : 11/306504
DATED            : July 3, 2007
INVENTOR(S)      : Anders Berkenstam et al.

It is certified that error appears in the above-identified patent and that said Letters Patent is hereby corrected as shown below:

On the title page item 62, the words "now abandoned" should be deleted, and line 62 should be revised to read: --Division of application No. 09/896,791, filed on Jun. 29, 2001--.

Signed and Sealed this

Thirtieth Day of September, 2008

JON W. DUDAS
*Director of the United States Patent and Trademark Office*

SEQUENCE LISTING

<160> NUMBER OF SEQ ID NOS: 3

<210> SEQ ID NO 1

-continued

```
<211> LENGTH: 460
<212> TYPE: DNA
<213> ORGANISM: Mus musculus
<220> FEATURE:
<221> NAME/KEY: misc_feature
<222> LOCATION: (1)...(460)
<223> OTHER INFORMATION: n = A,T,C or G

<400> SEQUENCE: 1
gccatggcgt tgggctgca gcgcgtgagg tcgaacaccg agctgcggaa ggagaagtcg        60
cgggaccgcc cgcagccggc gcacgaggag acggaggtgc tgtaccagct ggcgcacact      120
ctgccctttg cgcgcggcgt cacaccntnc tggacaaggc ctccatcatg cgcctcacaa      180
tcagctacct gcgcatgacc gcctctgcgc acagantgga aaaggggga gagccactgg      240 acgcctgcta cctgaaggcc ctggagggtt tcgtcatggt actcaccgcc gagggagaca      300
tggcttacct gtcggaaaat gtcagcaagc acctgggcct cagtcagtgg acctctgttc      360
ctcctccctg atacataacc ccactcctgg taccaatttc tctctggagc tcattggaca      420
cagtatcttt gattttatca tccctgtgac caagaggaac                            460

<210> SEQ ID NO 2
<211> LENGTH: 1100
<212> TYPE: DNA
<213> ORGANISM: Mus musculus
<220> FEATURE:
<221> NAME/KEY: CDS
<222> LOCATION: (19)...(939)

<400> SEQUENCE: 2
gaattcggca cgagggcc atg gcg ttg ggg ctg cag cgc gtg agg tcg aac        51
                   Met Ala Leu Gly Leu Gln Arg Val Arg Ser Asn
                    1               5                      10 acc gag ctg cgg aag gag aag tcg cgg gac gcg gcc cgc agc cgg cgc        99
Thr Glu Leu Arg Lys Glu Lys Ser Arg Asp Ala Ala Arg Ser Arg Arg
             15                  20                  25 agc cag gag acg gag gtg ctg tac cag ctg gcg cac act ctg ccc ttt       147
Ser Gln Glu Thr Glu Val Leu Tyr Gln Leu Ala His Thr Leu Pro Phe
         30                  35                  40 gcg cgc ggc gtc agc gcg cac ctg gac aag gcc tcc atc atg cgc ctc       195
Ala Arg Gly Val Ser Ala His Leu Asp Lys Ala Ser Ile Met Arg Leu
     45                  50                  55 aca atc agc tac ctg cgc atg cac cgc ctc tgc gca gca ggt gga aaa       243
Thr Ile Ser Tyr Leu Arg Met His Arg Leu Cys Ala Ala Gly Gly Lys
 60                  65                  70                  75 agg ggg aga gcc act gga cgc ctg cta cct gaa ggc cct gga ggg ttt       291
Arg Gly Arg Ala Thr Gly Arg Leu Leu Pro Glu Gly Pro Gly Gly Phe
                 80                  85                  90 cgt cat ggt act cac cgc cga ggg aga cat ggc tta cct gtc gga aaa       339
Arg His Gly Thr His Arg Arg Gly Arg His Gly Leu Pro Val Gly Lys
             95                 100                 105 tgt cag caa gca cct ggg cct cag tca gtg gac ctc tgt tcc tcc tcc       387
Cys Gln Gln Ala Pro Gly Pro Gln Ser Val Asp Leu Cys Ser Ser Ser
        110                 115                 120 ctg ata cat aac ccc act cct ggt acc aat ttc tct ctg gag ctc att       435
Leu Ile His Asn Pro Thr Pro Gly Thr Asn Phe Ser Leu Glu Leu Ile
    125                 130                 135 gga cac agt atc ttt gat ttt atc cat ccc tgt gac caa gag gaa ctt       483
Gly His Ser Ile Phe Asp Phe Ile His Pro Cys Asp Gln Glu Glu Leu
140                 145                 150                 155 caa gac gcc ctg acc ccc agg ccg aac ctg tca aag aag aag ctg gaa       531
Gln Asp Ala Leu Thr Pro Arg Pro Asn Leu Ser Lys Lys Lys Leu Glu
```

```
gcc cca aca gag cgc cac ttt tcc ctg cga atg aag agc acg ctc acc    579
Ala Pro Thr Glu Arg His Phe Ser Leu Arg Met Lys Ser Thr Leu Thr
            175                 180                 185 agc aga ggg cgc acg ctc aac ctc aaa gcg gcc acc tgg aag gtg ctg    627
Ser Arg Gly Arg Thr Leu Asn Leu Lys Ala Ala Thr Trp Lys Val Leu
            190                 195                 200 cac tgc tca gga cat atg agg gcc tac aag ccc cct gca cag act tcc    675
His Cys Ser Gly His Met Arg Ala Tyr Lys Pro Pro Ala Gln Thr Ser
            205                 210                 215 cct gcc ggg agc cct cgc tcc gag cct ccc ctg caa tgc ctg gtg ctt    723
Pro Ala Gly Ser Pro Arg Ser Glu Pro Pro Leu Gln Cys Leu Val Leu
220                 225                 230                 235 atc tgt gaa gcc atc ccc cag ctc ccc ttc cac gat ggt gct act ctg    771
Ile Cys Glu Ala Ile Pro Gln Leu Pro Phe His Asp Gly Ala Thr Leu
                240                 245                 250 ggt ctt cca cag gag aag act ccc atc tct acc tta ttc acc cct ctt    819
Gly Leu Pro Gln Glu Lys Thr Pro Ile Ser Thr Leu Phe Thr Pro Leu
                255                 260                 265 tgg aag gca cta ctt tgt ctt gtc aag agg tgg cct gtt cag gtg cta    867
Trp Lys Ala Leu Leu Cys Leu Val Lys Arg Trp Pro Val Gln Val Leu
                270                 275                 280 cag ggg aaa ggg act gaa tcc tct ctc ccc tca tgg gtg ttg tgg gcc    915
Gln Gly Lys Gly Thr Glu Ser Ser Leu Pro Ser Trp Val Leu Trp Ala
285                 290                 295 ctt aac cgg aaa aat tgt cct ggc tag gagggagtga aggacatggc          962
Leu Asn Arg Lys Asn Cys Pro Gly
300                 305 ccagctatcc ttagcccaga aacccacaaa tgtctccaaa accaccataa agacctctcc  1022
ttgttaggca ccagagaaaa aaaaaaaaaa aaaaaaaaaa aaaaaaaaaa aaaaaaaaaa  1082
aaaaaaacat gcggccgc                                               1100

<210> SEQ ID NO 3
<211> LENGTH: 307
<212> TYPE: PRT
<213> ORGANISM: Mus musculus

<400> SEQUENCE: 3

Met Ala Leu Gly Leu Gln Arg Val Arg Ser Asn Thr Glu Leu Arg Lys
1               5                   10                  15

Glu Lys Ser Arg Asp Ala Ala Arg Ser Arg Arg Ser Gln Glu Thr Glu
            20                  25                  30

Val Leu Tyr Gln Leu Ala His Thr Leu Pro Phe Ala Arg Gly Val Ser
        35                  40                  45

Ala His Leu Asp Lys Ala Ser Ile Met Arg Leu Thr Ile Ser Tyr Leu
    50                  55                  60

Arg Met His Arg Leu Cys Ala Ala Gly Lys Arg Gly Arg Ala Thr
65                  70                  75                  80

Gly Arg Leu Leu Pro Glu Gly Pro Gly Gly Phe Arg His Gly Thr His
                85                  90                  95

Arg Arg Gly Arg His Gly Leu Pro Val Gly Lys Cys Gln Gln Ala Pro
            100                 105                 110

Gly Pro Gln Ser Val Asp Leu Cys Ser Ser Ser Leu Ile His Asn Pro
        115                 120                 125

Thr Pro Gly Thr Asn Phe Ser Leu Glu Leu Ile Gly His Ser Ile Phe
    130                 135                 140
```

-continued

```
Asp Phe Ile His Pro Cys Asp Gln Glu Leu Gln Asp Ala Leu Thr
145                 150                 155                 160

Pro Arg Pro Asn Leu Ser Lys Lys Leu Glu Ala Pro Thr Glu Arg
            165                 170                 175

His Phe Ser Leu Arg Met Lys Ser Thr Leu Thr Ser Arg Gly Arg Thr
            180                 185                 190

Leu Asn Leu Lys Ala Ala Thr Trp Lys Val Leu His Cys Ser Gly His
            195                 200                 205

Met Arg Ala Tyr Lys Pro Pro Ala Gln Thr Ser Pro Ala Gly Ser Pro
        210                 215                 220

Arg Ser Glu Pro Pro Leu Gln Cys Leu Val Leu Ile Cys Glu Ala Ile
225                 230                 235                 240

Pro Gln Leu Pro Phe His Asp Gly Ala Thr Leu Gly Leu Pro Gln Glu
            245                 250                 255

Lys Thr Pro Ile Ser Thr Leu Phe Thr Pro Leu Trp Lys Ala Leu Leu
            260                 265                 270

Cys Leu Val Lys Arg Trp Pro Val Gln Val Leu Gln Gly Lys Gly Thr
        275                 280                 285

Glu Ser Ser Leu Pro Ser Trp Val Leu Trp Ala Leu Asn Arg Lys Asn
    290                 295                 300

Cys Pro Gly
305
```